United States Patent
Lion et al.

(10) Patent No.: US 10,617,626 B2
(45) Date of Patent: Apr. 14, 2020

(54) PROCESS FOR TREATING KERATIN FIBRES WITH AN ETHYLENIC POLYMER BEARING A MALEIC ANHYDRIDE GROUP AND A POLYOL

(71) Applicant: L'OREAL, Paris (FR)

(72) Inventors: Bertrand Lion, Aulnay-sous-bois (FR); Julien Portal, Aulnay-sous-bois (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/064,051

(22) PCT Filed: Dec. 16, 2016

(86) PCT No.: PCT/EP2016/081359
§ 371 (c)(1),
(2) Date: Jun. 20, 2018

(87) PCT Pub. No.: WO2017/108603
PCT Pub. Date: Jun. 29, 2017

(65) Prior Publication Data
US 2019/0000744 A1    Jan. 3, 2019

(30) Foreign Application Priority Data
Dec. 22, 2015   (FR) ..................... 15 63119

(51) Int. Cl.
*A61K 8/34* (2006.01)
*A61K 8/41* (2006.01)
*A61K 8/81* (2006.01)
*A61Q 5/06* (2006.01)

(52) U.S. Cl.
CPC ............ *A61K 8/8164* (2013.01); *A61K 8/345* (2013.01); *A61K 8/41* (2013.01); *A61Q 5/06* (2013.01); *A61K 2800/54* (2013.01)

(58) Field of Classification Search
None
See application file for complete search history.

(56) References Cited

U.S. PATENT DOCUMENTS

| | | |
|---|---|---|
| 5,185,143 A | 2/1993 | Cohen |
| 2007/0238807 A1 | 10/2007 | Safir et al. |
| 2013/0309190 A1* | 11/2013 | Dimotakis ............... A61Q 5/06 424/70.17 |
| 2014/0227210 A1* | 8/2014 | Farcet .................. A61K 8/8152 424/59 |

FOREIGN PATENT DOCUMENTS

EP   2 582 057 A1   1/2011

* cited by examiner

*Primary Examiner* — Brian Gulledge
(74) *Attorney, Agent, or Firm* — Polsinelli PC

(57) ABSTRACT

Process for treating keratin fibres with an ethylenicpolymer bearing a maleic anhydride group and a polyol The invention relates to a cosmetic process for treating keratin fibres, comprising the application to the keratin fibres of a mixture of a maleic anhydride ethylenic polymer, a liposoluble polyol and an amine catalyst; said maleic anhydride ethylenic polymer being obtained by polymerization of: (a) 25% to 95% by weight, relative to the total weight of monomers, of an ethylenic monomer bearing an at least C8 linear or branched alkyl group; (b) 5% to 25% by weight of maleic anhydride; (c) 0% to 50% by weight of additional (meth) acrylate monomer; and a step of heating the keratin fibres to a temperature ranging from 90° C. to 250° C. The invention also relates to the crosslinked polymer obtained by reacting said ethylenic polymer with said liposoluble polyol. The treated keratin fibres have good water-resistant fixing properties.

30 Claims, No Drawings

PROCESS FOR TREATING KERATIN FIBRES WITH AN ETHYLENIC POLYMER BEARING A MALEIC ANHYDRIDE GROUP AND A POLYOL

CROSS REFERENCE TO RELATED APPLICATIONS

This application is the National Phase of Application No. PCT/EP2016/081359 filed Dec. 16, 2016, which claims priority to Application No. 15 63119 filed in France on Dec. 22, 2015 under 35 U.S.C. § 119. The entire contents of each application are hereby incorporated by reference.

The present invention relates to a cosmetic process for treating keratin fibres using an ethylenic polymer bearing maleic anhydride groups and a liposoluble polyol, and also to a kit for performing said process.

Hair products generally contain film-forming polymers to give the hair good hairstyle hold. However, the quality of the hair hold may be impaired on contact with water, for example rain or when showering: this impairment may be due to the fact that the deposit of the film-forming polymer on the hair has poor resistance to contact with water and is removed over time.

The aim of the present invention is to provide a polymer for obtaining a film-forming deposit that has good water resistance and that is suitable for application to the hair to obtain good fixing properties.

The inventors have discovered that a particular maleic anhydride ethylenic polymer combined with a particular polyol, applied to the hair, affords good hair-fixing properties, with good water resistance.

More precisely, a subject of the present invention is a process, especially a cosmetic process, for treating keratin fibres, comprising:
(i) a step of applying to keratin fibres a mixture (extemporaneous) of a maleic anhydride block polymer, or of a cosmetic composition comprising it, of a liposoluble polyol compound or of a cosmetic composition containing it, and of an amine catalyst; said maleic anhydride ethylenic polymer being derived from the polymerization of:
(a) 45% to 95% by weight, relative to the total weight of monomers, of an ethylenic monomer bearing an at least C8 linear or branched alkyl group;
(b) 5% to 25% by weight of maleic anhydride;
(c) 0 to 50% by weight of additional monomer chosen from:
(i) polydimethylsiloxane silicone monomers bearing a mono (meth)acryloyloxy end group as defined below;
(ii) linear or branched C1-C6 alkyl (meth)acrylate or C6-C12 cycloalkyl (meth)acrylate non-silicone monomers;
(ii) a step of heating the keratin fibres to a temperature ranging from 90° C. to 250° C.; steps (i) and (ii) being performed at the same time or separately, in the order (i) and then (ii).

A subject of the invention is also a composition, especially a cosmetic composition, obtained by mixing a composition comprising said maleic anhydride ethylenic polymer or a composition containing it and comprising a physiologically acceptable medium, a liposoluble polyol compound or a composition containing it and comprising a physiologically acceptable medium, and an amine catalyst, as defined below.

A subject of the invention is also a kit comprising:
a first composition comprising said maleic anhydride ethylenic polymer as described previously and optionally comprising a physiologically acceptable medium, and a second composition comprising a liposoluble polyol compound and optionally comprising a physiologically acceptable medium,
the first composition or the second composition also comprising said amine catalyst,
the first and second compositions each being packaged in a separate packaging assembly.

The composition packaging assembly is, in a known manner, any packaging that is suitable for storing cosmetic compositions (especially a bottle, tube, spray bottle or aerosol bottle).

Such a kit allows the process for treating keratin fibres according to the invention to be performed.

The maleic anhydride ethylenic polymer used according to the invention comprises a maleic anhydride ethylenic monomer and optionally an additional monomer as defined previously. Advantageously, the maleic anhydride ethylenic polymer is formed essentially from these monomers in the contents described previously.

Such a copolymer is referred to hereinbelow as an ethylenic polymer.

The ethylenic polymer used according to the invention comprises an ethylenic monomer bearing an at least C8 linear or branched alkyl group (referred to as a fatty-chain ethylenic monomer); said alkyl group may be a linear or branched C8-C22 or C8 to C12 alkyl group.

Such a fatty-chain ethylenic monomer may be chosen from:
a) linear or branched C8-C22 alkyl (meth)acrylates (i.e. comprising a C8-C22 alkyl group);
b) the (meth)acrylamides of formula $CH_2=C(R1)-CONR3R4$ in which R1 represents a hydrogen atom or a methyl radical, R3 represents a hydrogen atom or a linear or branched C1-C12 alkyl group, and R4 represents a linear or branched C8 to C12 alkyl group, such as an isooctyl, isononyl or undecyl group;
c) the vinyl esters of formula $R5-CO-O-CH=CH_2$ in which R5 represents a linear or branched C8-C22 alkyl group;
d) the ethers of formula $R6-O-CH=CH_2$ in which R6 represents a linear or branched C8-C22 alkyl group.

Linear or branched C8-C22 alkyl groups that may be mentioned include octyl, 2-ethylhexyl, isooctyl, nonyl, decyl, undecyl, lauryl, myristyl, palmityl, stearyl, eicosyl and behenyl radicals, and especially a 2-ethylhexyl, lauryl, behenyl or stearyl group.

Preferably, the fatty-chain ethylenic monomer is chosen from C8-C22 and especially C8-C18 alkyl (meth)acrylates, for instance 2-ethylhexyl acrylate, 2-ethylhexyl methacrylate, lauryl acrylate, lauryl methacrylate, behenyl acrylate, behenyl methacrylate, stearyl acrylate and stearyl methacrylate.

2-Ethylhexyl acrylate, 2-ethylhexyl methacrylate, stearyl acrylate or stearyl methacrylate is preferably used.

2-Ethylhexyl acrylate is preferentially used.

The fatty-chain monomer may be present in said ethylenic polymer in a content ranging from 45% to 90% by weight and preferably ranging from 50% to 90% by weight, relative to the total weight of monomers.

In the absence of additional monomer in the ethylenic polymer, the fatty-chain monomer may be present in a content ranging from 75% to 95% by weight, preferably ranging from 75% to 90% by weight and preferentially ranging from 78% to 87% by weight, relative to the total weight of monomers.

In the presence of additional monomer in the ethylenic polymer, the fatty-chain monomer may be present in a content ranging from 45% to 94.5% by weight, preferably ranging from 45% to 90% by weight, preferentially ranging from 50% to 75% by weight and more preferentially ranging from 52% to 67% by weight, relative to the total weight of monomers.

The ethylenic polymer used according to the invention contains maleic anhydride.

Maleic anhydride may be present in said ethylenic polymer in a content ranging from 10% to 25% by weight and preferably ranging from 13% to 22% by weight, relative to the total weight of monomers.

The additional silicone monomer is a polydimethylsiloxane bearing a mono(meth)acryloyloxy end group of formula (I) (referred to hereinbelow as a silicone monomer) below:

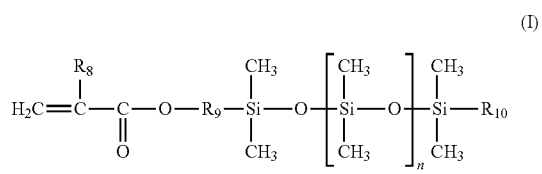

in which:
- R8 denotes a hydrogen atom or a methyl group; preferably methyl;
- R9 denotes a linear or branched, preferably linear, divalent hydrocarbon-based group containing from 1 to 10 carbon atoms, preferably containing from 2 to 4 carbon atoms, and optionally containing one or two —O— ether bonds; preferably an ethylene, propylene or butylene group;
- R10 denotes a linear or branched alkyl group containing from 1 to 10 carbon atoms, especially from 2 to 8 carbon atoms; preferably methyl, ethyl, propyl, butyl or pentyl;
- n denotes an integer ranging from 1 to 300, preferably ranging from 3 to 200 and preferentially ranging from 5 to 100.

Use may be made in particular of monomethacryloyloxypropyl polydimethylsiloxanes such as those sold under the names MCR-M07, MCR-M17, MCR-M11 and MCR-M22 by Gelest Inc or the silicone macromonomers sold under the names X-22-2475, X-22-2426 and X-22-174DX by Shin-Etsu.

The additional silicone monomer may be present in said ethylenic polymer in a content ranging from 5% to 50% by weight, relative to the total weight of monomers, preferably ranging from 15% to 40% by weight, preferentially ranging from 20% to 35% by weight and especially ranging from 25% to 35% by weight.

The additional non-silicone monomer chosen from linear or branched C1-C6 alkyl (meth) acrylates may be, for example, methyl (meth)acrylate, ethyl (meth)acrylate, propyl (meth)acrylate, n-butyl (meth)acrylate, isobutyl (meth)acrylate, pentyl (meth)acrylate or hexyl (meth)acrylate. Methyl (meth)acrylate or ethyl (meth)acrylate is preferably used.

The C6-C12 cycloalkyl (meth)acrylate is preferably isobornyl (meth)acrylate.

The additional non-silicone monomer may be present in said ethylenic polymer in a content ranging from 0.5% to 50% by weight, relative to the total weight of monomers, preferably ranging from 5% to 50% by weight, preferentially ranging from 15% to 40% by weight and more preferentially ranging from 20% to 35% by weight.

According to one embodiment of the invention, the ethylenic polymer does not comprise any additional monomer: it is formed from ethylenic monomer bearing an at least C8 linear or branched alkyl group and maleic anhydride.

According to another embodiment of the invention, the ethylenic polymer comprises at least one additional monomer as defined previously. The additional monomer may be present in said ethylenic polymer in a content ranging from 5% to 50% by weight, relative to the total weight of monomers, preferably ranging from 15% to 40% by weight, preferentially ranging from 20% to 35% by weight and especially ranging from 25% to 35% by weight.

According to another embodiment of the invention, the ethylenic polymer comprises at least one additional silicone monomer as defined previously.

According to another embodiment of the invention, the ethylenic polymer comprises at least one additional non-silicone monomer as defined previously. Preferably, it is a C6-C12 cycloalkyl (meth)acrylate.

According to another embodiment of the invention, the ethylenic polymer comprises at least one additional silicone monomer and at least one additional non-silicone monomer as defined previously.

According to a first embodiment of the invention, the ethylenic polymer comprises, or consists of:
(a) 75% to 95% by weight, relative to the total weight of monomers, of linear or branched C8-C22 alkyl (meth)acrylate;
(b) 5% to 25% by weight of maleic anhydride.

The ethylenic polymer especially comprises, or consists of:
(a) 75% to 95% by weight, relative to the total weight of monomers, of linear or branched C8-C18 alkyl (meth)acrylate;
(b) 5% to 25% by weight of maleic anhydride.

In particular, the ethylenic polymer comprises, or consists of:
(a) 75% to 95% by weight, relative to the total weight of monomers, of 2-ethylhexyl (meth)acrylate;
(b) 5% to 25% by weight of maleic anhydride.

In particular, the ethylenic polymer comprises, or consists of:
(a) 75% to 95% by weight, relative to the total weight of monomers, of stearyl (meth)acrylate;
(b) 5% to 25% by weight of maleic anhydride.

In particular, the ethylenic polymer comprises, or consists of:
(a) 75% to 95% by weight, relative to the total weight of monomers, of a mixture of 2-ethylhexyl (meth)acrylate and of stearyl (meth)acrylate;
(b) 5% to 25% by weight of maleic anhydride.

Preferably, the ethylenic polymer comprises, or consists of:
(a) 75% to 90% by weight, relative to the total weight of monomers, of linear or branched C8-C22 alkyl (meth)acrylate;
(b) 10% to 25% by weight of maleic anhydride.

The ethylenic polymer especially comprises, or consists of:
(a) 75% to 90% by weight, relative to the total weight of monomers, of linear or branched C8-C18 alkyl (meth)acrylate;
(b) 10% to 25% by weight of maleic anhydride.

In particular, the ethylenic polymer comprises, or consists of:
(a) 75% to 90% by weight, relative to the total weight of monomers, of 2-ethylhexyl (meth)acrylate;

(b) 10% to 25% by weight of maleic anhydride.

In particular, the ethylenic polymer comprises, or consists of:
(a) 75% to 90% by weight, relative to the total weight of monomers, of stearyl (meth)acrylate);
(b) 10% to 25% by weight of maleic anhydride.

In particular, the ethylenic polymer comprises, or consists of:
(a) 75% to 90% by weight, relative to the total weight of monomers, of a mixture of 2-ethylhexyl (meth)acrylate and of stearyl (meth)acrylate;
(b) 10% to 25% by weight of maleic anhydride.

Preferentially, the ethylenic polymer comprises, or consists of:
(a) 78% to 87% by weight, relative to the total weight of monomers, of linear or branched C8-C22 alkyl (meth) acrylate;
(b) 13% to 22% by weight of maleic anhydride.

The ethylenic polymer especially comprises, or consists of:
(a) 78% to 87% by weight, relative to the total weight of monomers, of linear or branched C8-C18 alkyl (meth) acrylate;
(b) 13% to 22% by weight of maleic anhydride.

In particular, the ethylenic polymer comprises, or consists of:
(a) 78% to 87% by weight, relative to the total weight of monomers, of 2-ethylhexyl (meth)acrylate;
(b) 13% to 22% by weight of maleic anhydride.

In particular, the ethylenic polymer comprises, or consists of:
(a) 78% to 87% by weight, relative to the total weight of monomers, of stearyl (meth)acrylate);
(b) 13% to 22% by weight of maleic anhydride.

In particular, the ethylenic polymer comprises, or consists of:
(a) 78% to 87% by weight, relative to the total weight of monomers, of a mixture of 2-ethylhexyl (meth)acrylate and of stearyl (meth)acrylate;
(b) 13% to 22% by weight of maleic anhydride.

The ethylenic polymer may be chosen from the following copolymers:
2-ethylhexyl acrylate/maleic anhydride
stearyl acrylate/maleic anhydride
2-ethylhexyl acrylate/stearyl acrylate/maleic anhydride
in the respective monomer contents described previously; and in particular:
2-ethylhexyl acrylate/maleic anhydride (85/15 by weight)
2-ethylhexyl acrylate/maleic anhydride (80/20 by weight)
2-ethylhexyl acrylate/stearyl acrylate/maleic anhydride (50/30/20 by weight).

According to a second embodiment of the invention, the ethylenic polymer comprises, or consists of:
(a) 45% to 94.5% by weight, relative to the total weight of monomers, of linear or branched C8-C22 alkyl (meth) acrylate;
(b) 5% to 25% by weight of maleic anhydride;
(c) 0.5% to 50% by weight of silicone monomer (I) as described previously.

The ethylenic polymer especially comprises, or consists of:
(a) 45% to 94.5% by weight, relative to the total weight of monomers, of linear or branched C8-C18 alkyl (meth) acrylate;
(b) 5% to 25% by weight of maleic anhydride;
(c) 0.5% to 50% by weight of silicone monomer (I) as described previously.

In particular, the ethylenic polymer comprises, or consists of:
(a) 45% to 94.5% by weight, relative to the total weight of monomers, of 2-ethylhexyl (meth)acrylate;
(b) 5% to 25% by weight of maleic anhydride;
(c) 0.5% to 50% by weight of silicone monomer (I) as described previously.

In particular, the ethylenic polymer comprises, or consists of:
(a) 45% to 94.5% by weight, relative to the total weight of monomers, of sterile (meth)acrylate);
(b) 5% to 25% by weight of maleic anhydride;
(c) 0.5% to 50% by weight of silicone monomer (I) as described previously.

In particular, the ethylenic polymer comprises, or consists of:
(a) 45% to 94.5% by weight, relative to the total weight of monomers, of a mixture of 2-ethylhexyl (meth)acrylate and of stearyl (meth)acrylate;
(b) 5% to 25% by weight of maleic anhydride;
(c) 0.5% to 50% by weight of silicone monomer (I) as described previously.

Preferably, the ethylenic polymer comprises, or consists of:
(a) 45% to 90% by weight, relative to the total weight of monomers, of linear or branched C8-C22 alkyl (meth) acrylate;
(b) 5% to 25% by weight of maleic anhydride;
(c) 5% to 50% by weight of silicone monomer (I) as described previously.

The ethylenic polymer especially comprises, or consists of:
(a) 45% to 90% by weight, relative to the total weight of monomers, of linear or branched C8-C18 alkyl (meth) acrylate;
(b) 5% to 25% by weight of maleic anhydride;
(c) 5% to 50% by weight of silicone monomer (I) as described previously.

In particular, the ethylenic polymer comprises, or consists of:
(a) 45% to 90% by weight, relative to the total weight of monomers, of 2-ethylhexyl (meth)acrylate;
(b) 5% to 25% by weight of maleic anhydride;
(c) 5% to 50% by weight of silicone monomer (I) as described previously.

In particular, the ethylenic polymer comprises, or consists of:
(a) 45% to 90% by weight, relative to the total weight of monomers, of sterile (meth)acrylate);
(b) 5% to 25% by weight of maleic anhydride;
(c) 5% to 50% by weight of silicone monomer (I) as described previously.

In particular, the ethylenic polymer comprises, or consists of:
(a) 45% to 90% by weight, relative to the total weight of monomers, of a mixture of 2-ethylhexyl (meth)acrylate and of stearyl (meth)acrylate;
(b) 5% to 25% by weight of maleic anhydride;
(c) 5% to 50% by weight of silicone monomer (I) as described previously.

Preferentially, the ethylenic polymer comprises, or consists of:
(a) 50% to 75% by weight, relative to the total weight of monomers, of linear or branched C8-C22 alkyl (meth) acrylate;
(b) 10% to 25% by weight of maleic anhydride;

(c) 15% to 40% by weight of silicone monomer (I) as described previously.

The ethylenic polymer especially comprises, or consists of:
(a) 50% to 75% by weight, relative to the total weight of monomers, of linear or branched C8-C18 alkyl (meth)acrylate;
(b) 10% to 25% by weight of maleic anhydride;
(c) 15% to 40% by weight of silicone monomer (I) as described previously.

In particular, the ethylenic polymer comprises, or consists of:
(a) 50% to 75% by weight, relative to the total weight of monomers, of 2-ethylhexyl (meth)acrylate;
(b) 10% to 25% by weight of maleic anhydride;
(c) 15% to 40% by weight of silicone monomer (I) as described previously.

In particular, the ethylenic polymer comprises, or consists of:
(a) 50% to 75% by weight, relative to the total weight of monomers, of sterile (meth)acrylate);
(b) 10% to 25% by weight of maleic anhydride;
(c) 15% to 40% by weight of silicone monomer (I) as described previously.

In particular, the ethylenic polymer comprises, or consists of:
(a) 50% to 75% by weight, relative to the total weight of monomers, of a mixture of 2-ethylhexyl (meth)acrylate and of stearyl (meth)acrylate;
(b) 10% to 25% by weight of maleic anhydride;
(c) 15% to 40% by weight of silicone monomer (I) as described previously.

More preferentially, the ethylenic polymer comprises, or consists of:
(a) 52% to 67% by weight, relative to the total weight of monomers, of linear or branched C8-C22 alkyl (meth)acrylate;
(b) 13% to 22% by weight of maleic anhydride;
(c) 20% to 35% by weight of silicone monomer (I) as described previously.

The ethylenic polymer especially comprises, or consists of:
(a) 52% to 67% by weight, relative to the total weight of monomers, of linear or branched C8-C18 alkyl (meth)acrylate;
(b) 13% to 22% by weight of maleic anhydride;
(c) 20% to 35% by weight of silicone monomer (I) as described previously.

In particular, the ethylenic polymer comprises, or consists of:
(a) 52% to 67% by weight, relative to the total weight of monomers, of 2-ethylhexyl (meth)acrylate;
(b) 13% to 22% by weight of maleic anhydride;
(c) 20% to 35% by weight of silicone monomer (I) as described previously.

In particular, the ethylenic polymer comprises, or consists of:
(a) 52% to 67% by weight, relative to the total weight of monomers, of sterile (meth)acrylate);
(b) 13% to 22% by weight of maleic anhydride;
(c) 20% to 35% by weight of silicone monomer (I) as described previously.

In particular, the ethylenic polymer comprises, or consists of:
(a) 52% to 67% by weight, relative to the total weight of monomers, of a mixture of 2-ethylhexyl (meth)acrylate and of stearyl (meth)acrylate;
(b) 13% to 22% by weight of maleic anhydride;
(c) 20% to 35% by weight of silicone monomer (I) as described previously.

The ethylenic polymer may be chosen from the following copolymers:
2-ethylhexyl acrylate/maleic anhydride/silicone monomer (I)
stearyl acrylate/maleic anhydride/silicone monomer (I)
2-ethylhexyl acrylate/stearyl acrylate/maleic anhydride/silicone monomer (I)
in the respective monomer contents described previously; and in particular:
the 2-ethylhexyl acrylate/PDMS methacrylate/maleic anhydride copolymer (50/30/20 by weight).

According to a third embodiment of the invention, the ethylenic polymer comprises, or consists of:
(a) 45% to 94.5% by weight, relative to the total weight of monomers, of linear or branched C8-C22 alkyl (meth)acrylate;
(b) 5% to 25% by weight of maleic anhydride;
(c) 0.5% to 50% by weight of additional non-silicone monomer chosen from linear or branched C1-C6 alkyl (meth)acrylates or C6-C12 cycloalkyl (meth)acrylates.

The ethylenic polymer especially comprises, or consists of:
(a) 45% to 94.5% by weight, relative to the total weight of monomers, of linear or branched C8-C18 alkyl (meth)acrylate;
(b) 5% to 25% by weight of maleic anhydride;
(c) 0.5% to 50% by weight of C6-C12 cycloalkyl (meth)acrylate.

In particular, the ethylenic polymer comprises, or consists of:
(a) 45% to 94.5% by weight, relative to the total weight of monomers, of 2-ethylhexyl (meth)acrylate;
(b) 5% to 25% by weight of maleic anhydride;
(c) 0.5% to 50% by weight of isobornyl (meth)acrylate.

In particular, the ethylenic polymer comprises, or consists of:
(a) 45% to 94.5% by weight, relative to the total weight of monomers, of sterile (meth)acrylate);
(b) 5% to 25% by weight of maleic anhydride;
(c) 0.5% to 50% by weight of isobornyl (meth)acrylate.

In particular, the ethylenic polymer comprises, or consists of:
(a) 45% to 94.5% by weight, relative to the total weight of monomers, of a mixture of 2-ethylhexyl (meth)acrylate and of stearyl (meth)acrylate;
(b) 5% to 25% by weight of maleic anhydride;
(c) 0.5% to 50% by weight of isobornyl (meth)acrylate.

Preferably, the ethylenic polymer comprises, or consists of:
(a) 45% to 90% by weight, relative to the total weight of monomers, of linear or branched C8-C22 alkyl (meth)acrylate;
(b) 5% to 25% by weight of maleic anhydride;
(c) 5% to 50% by weight of additional non-silicone monomer chosen from linear or branched C1-C6 alkyl (meth)acrylates or C6-C12 cycloalkyl (meth)acrylates.

The ethylenic polymer especially comprises, or consists of:
(a) 45% to 90% by weight, relative to the total weight of monomers, of linear or branched C8-C18 alkyl (meth)acrylate;
(b) 5% to 25% by weight of maleic anhydride;
(c) 5% to 50% by weight of C6-C12 cycloalkyl (meth)acrylate.

In particular, the ethylenic polymer comprises, or consists of:
(a) 45% to 90% by weight, relative to the total weight of monomers, of 2-ethylhexyl (meth)acrylate;
(b) 5% to 25% by weight of maleic anhydride;
(c) 5% to 50% by weight of isobornyl (meth)acrylate.

In particular, the ethylenic polymer comprises, or consists of:
(a) 45% to 90% by weight, relative to the total weight of monomers, of sterile (meth)acrylate);
(b) 5% to 25% by weight of maleic anhydride;
(c) 5% to 50% by weight of isobornyl (meth)acrylate.

In particular, the ethylenic polymer comprises, or consists of:
(a) 45% to 90% by weight, relative to the total weight of monomers, of a mixture of 2-ethylhexyl (meth)acrylate and of stearyl (meth)acrylate;
(b) 5% to 25% by weight of maleic anhydride;
(c) 5% to 50% by weight of isobornyl (meth)acrylate.

Preferentially, the ethylenic polymer comprises, or consists of:
(a) 50% to 75% by weight, relative to the total weight of monomers, of linear or branched C8-C22 alkyl (meth)acrylate;
(b) 10% to 25% by weight of maleic anhydride;
(c) 15% to 40% by weight of additional non-silicone monomer chosen from linear or branched C1-C6 alkyl (meth)acrylates or C6-C12 cycloalkyl (meth)acrylates.

The ethylenic polymer especially comprises, or consists of:
(a) 50% to 75% by weight, relative to the total weight of monomers, of linear or branched C8-C18 alkyl (meth)acrylate;
(b) 10% to 25% by weight of maleic anhydride;
(c) 15% to 40% by weight of C6-C12 cycloalkyl (meth)acrylate.

In particular, the ethylenic polymer comprises, or consists of:
(a) 50% to 75% by weight, relative to the total weight of monomers, of 2-ethylhexyl (meth)acrylate;
(b) 10% to 25% by weight of maleic anhydride;
(c) 15% to 40% by weight of isobornyl (meth)acrylate.

In particular, the ethylenic polymer comprises, or consists of:
(a) 50% to 75% by weight, relative to the total weight of monomers, of sterile (meth)acrylate);
(b) 10% to 25% by weight of maleic anhydride;
(c) 15% to 40% by weight of isobornyl (meth)acrylate.

In particular, the ethylenic polymer comprises, or consists of:
(a) 50% to 75% by weight, relative to the total weight of monomers, of a mixture of 2-ethylhexyl (meth)acrylate and of stearyl (meth)acrylate;
(b) 10% to 25% by weight of maleic anhydride;
(c) 15% to 40% by weight of isobornyl (meth)acrylate.

More preferentially, the ethylenic polymer comprises, or consists of:
(a) 52% to 67% by weight, relative to the total weight of monomers, of linear or branched C8-C22 alkyl (meth)acrylate;
(b) 13% to 22% by weight of maleic anhydride;
(c) 20% to 35% by weight of additional non-silicone monomer chosen from linear or branched C1-C6 alkyl (meth)acrylates or C6-C12 cycloalkyl (meth)acrylates.

The ethylenic polymer especially comprises, or consists of:
(a) 52% to 67% by weight, relative to the total weight of monomers, of linear or branched C8-C18 alkyl (meth)acrylate;
(b) 13% to 22% by weight of maleic anhydride;
(c) 20% to 35% by weight of C6-C12 cycloalkyl (meth)acrylate.

In particular, the ethylenic polymer comprises, or consists of:
(a) 52% to 67% by weight, relative to the total weight of monomers, of 2-ethylhexyl (meth)acrylate;
(b) 13% to 22% by weight of maleic anhydride;
(c) 20% to 35% by weight of isobornyl (meth)acrylate.

In particular, the ethylenic polymer comprises, or consists of:
(a) 52% to 67% by weight, relative to the total weight of monomers, of sterile (meth)acrylate);
(b) 13% to 22% by weight of maleic anhydride;
(c) 20% to 35% by weight of isobornyl (meth)acrylate.

In particular, the ethylenic polymer comprises, or consists of:
(a) 52% to 67% by weight, relative to the total weight of monomers, of a mixture of 2-ethylhexyl (meth)acrylate and of stearyl (meth)acrylate;
(b) 13% to 22% by weight of maleic anhydride;
(c) 20% to 35% by weight of isobornyl (meth)acrylate.

The ethylenic polymer may be chosen from the following copolymers:
2-ethylhexyl acrylate/maleic anhydride/isobornyl (meth)acrylate
stearyl acrylate/maleic anhydride/isobornyl (meth)acrylate
2-ethylhexyl acrylate/stearyl acrylate/maleic anhydride/isobornyl (meth)acrylate
in the respective monomer contents described previously.

According to a fourth embodiment of the invention, the ethylenic polymer comprises, or consists of:
(a) 45% to 94.5% by weight, relative to the total weight of monomers, of linear or branched C8-C22 alkyl (meth)acrylate;
(b) 5% to 25% by weight of maleic anhydride;
(c) 0.5% to 50% by weight of a mixture of additional non-silicone monomer chosen from C6-C12 cycloalkyl (meth)acrylates and of silicone monomer (I) as described previously.

The ethylenic polymer especially comprises, or consists of:
(a) 45% to 94.5% by weight, relative to the total weight of monomers, of linear or branched C8-C18 alkyl (meth)acrylate;
(b) 5% to 25% by weight of maleic anhydride;
(c) 0.5% to 50% by weight of a mixture of C6-C12 cycloalkyl (meth)acrylate and of silicone monomer (I) as described previously.

In particular, the ethylenic polymer comprises, or consists of:
(a) 45% to 94.5% by weight, relative to the total weight of monomers, of 2-ethylhexyl (meth)acrylate;
(b) 5% to 25% by weight of maleic anhydride;
(c) 0.5% to 50% by weight of a mixture of isobornyl (meth)acrylate and of silicone monomer (I) as described previously.

In particular, the ethylenic polymer comprises, or consists of:
(a) 45% to 94.5% by weight, relative to the total weight of monomers, of sterile (meth)acrylate);
(b) 5% to 25% by weight of maleic anhydride;

(c) 0.5% to 50% by weight of a mixture of isobornyl (meth)acrylate and of silicone monomer (I) as described previously.

In particular, the ethylenic polymer comprises, or consists of:
(a) 45% to 94.5% by weight, relative to the total weight of monomers, of a mixture of 2-ethylhexyl (meth)acrylate and of stearyl (meth)acrylate;
(b) 5% to 25% by weight of maleic anhydride;
(c) 0.5% to 50% by weight of a mixture of isobornyl (meth)acrylate and of silicone monomer (I) as described previously.

Preferably, the ethylenic polymer comprises, or consists of:
(a) 45% to 90% by weight, relative to the total weight of monomers, of linear or branched C8-C22 alkyl (meth)acrylate;
(b) 5% to 25% by weight of maleic anhydride;
(c) 5% to 50% by weight of a mixture of additional non-silicone monomer chosen from linear or branched C1-C6 alkyl (meth)acrylates or C6-C12 cycloalkyl (meth)acrylates and of silicone monomer (I) as described previously.

The ethylenic polymer especially comprises, or consists of:
(a) 45% to 90% by weight, relative to the total weight of monomers, of linear or branched C8-C18 alkyl (meth)acrylate;
(b) 5% to 25% by weight of maleic anhydride;
(c) 5% to 50% by weight of a mixture of C6-C12 cycloalkyl (meth)acrylate and of silicone monomer (I) as described previously.

In particular, the ethylenic polymer comprises, or consists of:
(a) 45% to 90% by weight, relative to the total weight of monomers, of 2-ethylhexyl (meth)acrylate;
(b) 5% to 25% by weight of maleic anhydride;
(c) 5% to 50% by weight of a mixture of isobornyl (meth)acrylate and of silicone monomer (I) as described previously.

In particular, the ethylenic polymer comprises, or consists of:
(a) 45% to 90% by weight, relative to the total weight of monomers, of sterile (meth)acrylate);
(b) 5% to 25% by weight of maleic anhydride;
(c) 5% to 50% by weight of a mixture of isobornyl (meth)acrylate and of silicone monomer (I) as described previously.

In particular, the ethylenic polymer comprises, or consists of:
(a) 45% to 90% by weight, relative to the total weight of monomers, of a mixture of 2-ethylhexyl (meth)acrylate and of stearyl (meth)acrylate;
(b) 5% to 25% by weight of maleic anhydride;
(c) 5% to 50% by weight of a mixture of isobornyl (meth)acrylate and of silicone monomer (I) as described previously.

Preferentially, the ethylenic polymer comprises, or consists of:
(a) 50% to 75% by weight, relative to the total weight of monomers, of linear or branched C8-C22 alkyl (meth)acrylate;
(b) 10% to 25% by weight of maleic anhydride;
(c) 15% to 40% by weight of a mixture of additional non-silicone monomer chosen from linear or branched C1-C6 alkyl (meth)acrylates or C6-C12 cycloalkyl (meth)acrylates and of silicone monomer (I) as described previously.

The ethylenic polymer especially comprises, or consists of:
(a) 50% to 75% by weight, relative to the total weight of monomers, of linear or branched C8-C18 alkyl (meth)acrylate;
(b) 10% to 25% by weight of maleic anhydride;
(c) 15% to 40% by weight of a mixture of C6-C12 cycloalkyl (meth)acrylate and of silicone monomer (I) as described previously.

In particular, the ethylenic polymer comprises, or consists of:
(a) 50% to 75% by weight, relative to the total weight of monomers, of 2-ethylhexyl (meth)acrylate;
(b) 10% to 25% by weight of maleic anhydride;
(c) 15% to 40% by weight of a mixture of isobornyl (meth)acrylate and of silicone monomer (I) as described previously.

In particular, the ethylenic polymer comprises, or consists of:
(a) 50% to 75% by weight, relative to the total weight of monomers, of sterile (meth)acrylate);
(b) 10% to 25% by weight of maleic anhydride;
(c) 15% to 40% by weight of a mixture of isobornyl (meth)acrylate and of silicone monomer (I) as described previously.

In particular, the ethylenic polymer comprises, or consists of:
(a) 50% to 75% by weight, relative to the total weight of monomers, of a mixture of 2-ethylhexyl (meth)acrylate and of stearyl (meth)acrylate;
(b) 10% to 25% by weight of maleic anhydride;
(c) 15% to 40% by weight of a mixture of isobornyl (meth)acrylate and of silicone monomer (I) as described previously.

More preferentially, the ethylenic polymer comprises, or consists of:
(a) 52% to 67% by weight, relative to the total weight of monomers, of linear or branched C8-C22 alkyl (meth)acrylate;
(b) 13% to 22% by weight of maleic anhydride;
(c) 20% to 35% by weight of a mixture of additional non-silicone monomer chosen from linear or branched C1-C6 alkyl (meth)acrylates or C6-C12 cycloalkyl (meth)acrylates and of silicone monomer (I) as described previously.

The ethylenic polymer especially comprises, or consists of:
(a) 52% to 67% by weight, relative to the total weight of monomers, of linear or branched C8-C18 alkyl (meth)acrylate;
(b) 13% to 22% by weight of maleic anhydride;
(c) 20% to 35% by weight of a mixture of C6-C12 cycloalkyl (meth)acrylate and of silicone monomer (I) as described previously.

In particular, the ethylenic polymer comprises, or consists of:
(a) 52% to 67% by weight, relative to the total weight of monomers, of 2-ethylhexyl (meth)acrylate;
(b) 13% to 22% by weight of maleic anhydride;
(c) 20% to 35% by weight of a mixture of isobornyl (meth)acrylate and of silicone monomer (I) as described previously.

In particular, the ethylenic polymer comprises, or consists of:
(a) 52% to 67% by weight, relative to the total weight of monomers, of sterile (meth)acrylate);
(b) 13% to 22% by weight of maleic anhydride;

(c) 20% to 35% by weight of a mixture of isobornyl (meth)acrylate and of silicone monomer (I) as described previously.

In particular, the ethylenic polymer comprises, or consists of:
(a) 52% to 67% by weight, relative to the total weight of monomers, of a mixture of 2-ethylhexyl (meth)acrylate and of stearyl (meth)acrylate;
(b) 13% to 22% by weight of maleic anhydride;
(c) 20% to 35% by weight of a mixture of isobornyl (meth)acrylate and of silicone monomer (I) as described previously.

The ethylenic polymer may be chosen from the following copolymers:
2-ethylhexyl acrylate/maleic anhydride/isobornyl (meth)acrylate/silicone monomer (I)
stearyl acrylate/maleic anhydride/isobornyl (meth)acrylate/silicone monomer (I)
2-ethylhexyl acrylate/stearyl acrylate/maleic anhydride/isobornyl (meth)acrylate/silicone monomer (I)
in the respective monomer contents described previously.

Advantageously, the polymer used according to the invention consists of the monomers described previously.

Advantageously, the polymer used according to the invention is nonionic.

Preferably, the maleic anhydride ethylenic polymer used according to the invention has a weight-average molecular weight ranging from 5000 to 1 000 000 g/mol, preferably ranging from 10 000 to 500 000 g/mol and preferentially ranging from 15 000 to 350 000 g/mol.

The molecular weight may especially be determined by steric exclusion chromatography, with THF eluent, polystyrene standard, 2414 refractometric detector from Waters.

The copolymer may be a random, alternating (block) or gradient polymer. Preferably, the copolymer is random.

The copolymer used according to the invention may be prepared by radical polymerization of the monomers described previously, especially as a mixture or added sequentially during the polymerization, especially using an organic solvent with a boiling point of greater than or equal to 60° C., for instance isododecane, ethanol, ethyl acetate, tetrahydrofuran, methyltetrahydrofuran or methyl ethyl ketone. The organic solvent makes it possible to dissolve the monomers used and the polymer formed.

The polymerization is especially performed in the presence of a radical initiator especially of peroxide type (for example tert-butyl peroxy-2-ethylhexanoate: Trigonox 21S; 2,5-dimethyl-2,5-bis(2-ethylhexanoylperoxy)hexane:Trigonox 141; tert-butyl peroxypivalate: Trigonox 25C75 from AkzoNobel) or of azo type, for example (AIBN: azobisisobutyronitrile; V50: 2,2'-azobis(2-amidinopropane) dihydrochloride).

The polymerization may be performed at a temperature ranging from 60 to 100° C., and preferably ranging from 60 to 85° C.

The polymerization time may be about 24 hours.

A subject of the invention is also the novel polymers derived from the polymerization of:
(a) 45% to 94.5% by weight, relative to the total weight of monomers, of linear or branched C8-C22 alkyl (meth)acrylate;
(b) 5% to 25% by weight of maleic anhydride monomer;
(c) 0.5% to 50% by weight of additional monomer chosen from:
(i) polydimethylsiloxane silicone monomers bearing a mono (meth)acryloyloxy end group as defined previously;
(ii) linear or branched C1-C6 alkyl (meth)acrylate or C6-C12 cycloalkyl (meth)acrylate non-silicone monomers;
and also similar polymers with the following preferred contents:
a) 75% to 95% and (b) 5% to 25%; (a) 75% to 90% and (b) 10% to 25%; (a) 78% to 87% and (b) 13% to 22%;
(a) 45% to 94.5% and (b) 5% to 25% and (c) 0.5% to 50%;
(a) 45% to 90% and (b) 5% to 25% and (c) 5% to 50%; (a) 50% to 75% and (b) 10% to 25% and (c) 15% to 40%; (a) 52% to 67% and (b) 13% to 22% and (c) 20% to 35%.

A subject of the invention is also the novel polymers described previously as second, third and fourth embodiments.

A subject of the invention is also the novel polymers derived from the polymerization of:
(a) 45% to 95% by weight, relative to the total weight of monomers, of an ethylenic monomer bearing an at least C8 linear or branched alkyl group chosen from:
i) the (meth)acrylamides of formula $CH_2=C(R1)$-$CONR3R4$ in which R1 represents a hydrogen atom or a methyl radical, R3 represents a hydrogen atom or a linear or branched C1-C12 alkyl group, and R4 represents a linear or branched C8 to C12 alkyl group, such as an isooctyl, isononyl or undecyl group;
ii) the vinyl esters of formula $R5-CO-O-CH=CH_2$ in which R5 represents a linear or branched C8-C22 alkyl group;
iii) the ethers of formula $R6-O-CH=CH_2$ in which R6 represents a linear or branched C8-C22 alkyl group;
(b) 5% to 25% by weight of maleic anhydride monomer;
(c) 0% to 50% by weight of additional monomer chosen from:
(i) linear or branched C1-C6 alkyl (meth)acrylate or C6-C12 cycloalkyl (meth)acrylate non-silicone monomers;
(ii) polydimethylsiloxane silicone monomers bearing a mono(meth)acryloyloxy end group as defined previously;
and also similar polymers with the following preferred contents:
a) 75% to 95% and (b) 5% to 25%; (a) 75% to 90% and (b) 10% to 25%; (a) 78% to 87% and (b) 13% to 22%;
(a) 45% to 94.5% and (b) 5% to 25% and (c) 0.5% to 50%;
(a) 45% to 90% and (b) 5% to 25% and (c) 5% to 50%; (a) 50% to 75% and (b) 10% to 25% and (c) 15% to 40%; (a) 52% to 67% and (b) 13% to 22% and (c) 20% to 35%.

The polymer used according to the invention may be used in a composition comprising a physiologically acceptable medium, in particular in a cosmetic composition.

The term "physiologically acceptable medium" means a medium that is compatible with human keratin fibres, in particular with the hair.

The term "cosmetic composition" means a composition that is compatible with keratin fibres, which has a pleasant colour, odour and feel and which does not cause any unacceptable discomfort (stinging, tautness or redness) liable to discourage the consumer from using it.

The maleic anhydride ethylenic polymer as defined previously may be present in the composition according to the invention in a content ranging from 0.1% to 40% by weight, relative to the total weight of the composition derived from the extemporaneous mixing, preferably from 0.5% to 35% by weight, preferentially ranging from 1% to 30% by weight and more preferentially ranging from 10% to 30% by weight.

The process according to the invention uses a liposoluble polyol compound.

The term "liposoluble polyol" means a polyhydroxylated compound that is soluble or miscible to at least 1% by weight in isododecane at 25° C.

The polyol used in the process according to the invention is an organic compound comprising at least two alcohol functions (i.e. two hydroxyl groups). This compound may comprise other unreactive chemical functions such as ester, amide, ketone or urethane functions.

It is possible to use a mixture of different polyols.

According to a first embodiment of the invention, the polyol compound is a non-polymeric organic compound of formula (II):

$$W(OH)n \qquad (II)$$

in which n denotes an integer greater than or equal to 2, preferably between 2 and 10, preferably between 2 and 5 (limits inclusive)
and W denotes a linear or branched or (hetero)cyclic, saturated or unsaturated C8-C30 multivalent (at least divalent) radical, W also possibly bearing one or more functions chosen from ether, thioether, ester, ketone and amide functions.

The term "non-polymeric compound" means a compound which is not directly obtained via a monomer polymerization reaction The polyol compound is preferably a diol compound.

Preferably, W denotes a C8-C18 multivalent radical, which is especially linear.

Preferentially, the liposoluble polyol is a C8-C18 diol, which is especially linear. Advantageously, the C8-C18 chain is a hydrocarbon-based chain (formed from carbon and hydrogen).

In particular, the liposoluble polyol is a C8-C16 and especially C10-C14 linear diol.

As polyol of formula (II), mention may be made of 1,8-octanediol, 1,10-decanediol, 1,12-dodecanediol, 1,14-tetradecanediol, 1,16-hexadecanediol and 1,18-octadecanediol.

1,10-Decanediol, 1,12-dodecanediol or 1,14-tetradecanediol is preferably used. 1,12-Dodecanediol is preferentially used.

According to a second embodiment of the invention, the polyol compound is a polymeric compound of formula (III):

$$POL(OH)m \qquad (III)$$

in which n denotes an integer greater than or equal to 2, and POL denotes a carbon-based or silicone polymeric radical, POL also possibly containing one or more heteroatoms such as 0, N or S, and/or one or more functions chosen from ester, ketone, amide, urea and carbamate functions, and/or possibly being substituted with one or more linear or branched C1-C10 alkyl or linear or branched C1-C10 alkoxy groups, it being understood that, when POL is substituted, the hydroxyl functions may be borne by the substituent(s).

The weight-average molecular weight of the polyol polymer compounds, such as those of formula (III), is generally between 500 and 400 000 and preferably between 500 and 150 000.

Preferably, the polymers (III) may be polymeric diols, especially polyolefin diols, polydimethylsiloxane diols or polyester diols.

The polyolefin diols may be polydienes bearing hydroxyl end groups, for instance those described in FR-A-2 782 723. They may be chosen from diols derived from polybutadiene, polyisoprene and poly(1,3-pentadiene) homopolymers and copolymers. Preferably, they have a number-average molecular mass (Mn) of less than 7000, preferably between 1000 and 5000. Mention will be made in particular of the hydroxylated polybutadienes sold by the company Cray Valley under the brand names Poly BD R45 HTLO, Poly BD R45V and Poly BD R-20 LM, which will preferably be used hydrogenated; and also hydrogenated dihydroxylated (1,2-polybutadienes), such as GI3000 of Mn=3100, GI2000 (Mn=2100) and GI1000 (Mn=1500) sold by the company Nisso.

Among the polyolefins with hydroxyl end groups, mention may be made preferentially of polyolefins, homopolymers or copolymers with α,ω-hydroxyl end groups, such as polyisobutylenes with α,ω-hydroxyl end groups; and the copolymers of formula:

$$HO - \!\!-\!\![\!-\!(CH_2)_4\!-\!]_m\!-\!-[CH_2-CH]_n\!-\!OH \qquad (IV)$$
$$\qquad\qquad\qquad\qquad\qquad |$$
$$\qquad\qquad\qquad\qquad\qquad C_2H_5$$

especially those sold by Mitsubishi under the brand name Polytail.

Hydrogenated polybutadiene diols are preferably used.

The polydimethylsiloxane diols may be those of formula (IV):

$$\qquad\qquad CH_3 \qquad CH_3 \qquad CH_3 \qquad (IV)$$
$$\qquad\qquad | \qquad\quad | \qquad\quad |$$
$$HO-X-Si-O-[Si-O]_n-Si-X-OH$$
$$\qquad\qquad | \qquad\quad | \qquad\quad |$$
$$\qquad\qquad CH_3 \qquad CH_3 \qquad CH_3$$

in which:
R1=divalent C2-C6 alkylene group
X=covalent bond or group O—R2- with R2=C2-C6 alkylene
n=1 to 100, preferably 5 to 50 and preferentially from 10 to 30.

The polydimethylsiloxane diols used may be those sold under the names KF-6000, KF-6001, KF-6002 and KF-6003 by the company Shin-Etsu Chemicals.

The polydimethylsiloxane diol preferably used is that of formula (IVa):

$$\qquad\qquad\qquad\qquad CH_3 \qquad CH_3 \qquad\qquad\qquad (IVa)$$
$$\qquad\qquad\qquad\qquad | \qquad\quad |$$
$$HO-(CH_2)_2-O-(CH_2)_3-[Si-O]_{20}-Si-(CH_2)_3-O-(CH_2)_2-OH$$
$$\qquad\qquad\qquad\qquad | \qquad\quad |$$
$$\qquad\qquad\qquad\qquad CH_3 \qquad CH_3$$

Use may also be made of dimethiconols, which are polydimethylsiloxanes bearing OH end functions. An example that may be mentioned is the product sold under the name Xiameter PMX-1502 Fluid by the company Dow Corning.

The polyester diols may be chosen from those derived from the condensation reaction of a C8-C30 and preferably C8-C18 diol, such as 1,8-octanediol, 1,9-nonanediol, 2-methyl-1,8-octanediol, 1,10-decadediol, 1,12-dodecanediol, 1,14-tetradecadediol, 1,16-hexadecanediol or 1,18-octadecanediol;
and of a C4-C12 dicarboxylic acid such as phthalic acid, isophthalic acid, terephthalic acid, maleic acid, fumaric acid, adipic acid, sebacic acid, trimellitic acid, azelaic acid, succinic acid or glutaric acid.

Polyester polyols are especially described in patents U.S. Pat. No. 6,136,880 and EP 0 960 355. Examples of polyester diols that may be mentioned include 1,9-nonanediol/adipic acid copolymers such as those sold under the name Kurapol N-2010 by the company Kuraray.

The polyester polyols are preferably chosen from the hydrogenated polybutadiene diols and polydimethylsiloxane diols of formula (IV) or (IVa) described previously.

Advantageously, the liposoluble polyol compound is used in a mole ratio of OH group of the liposoluble polyol/maleic anhydride group of the ethylenic polymer ranging from 0.01 to 10, preferably ranging from 0.1 to 5, preferentially ranging from 0.1 to 2 and more preferentially ranging from 0.1 to 1.

On contact with the ethylenic polymer, the polyol compound reacts with the maleic anhydride functions to form a crosslinked polymer, for example in the following manner:

Scheme I

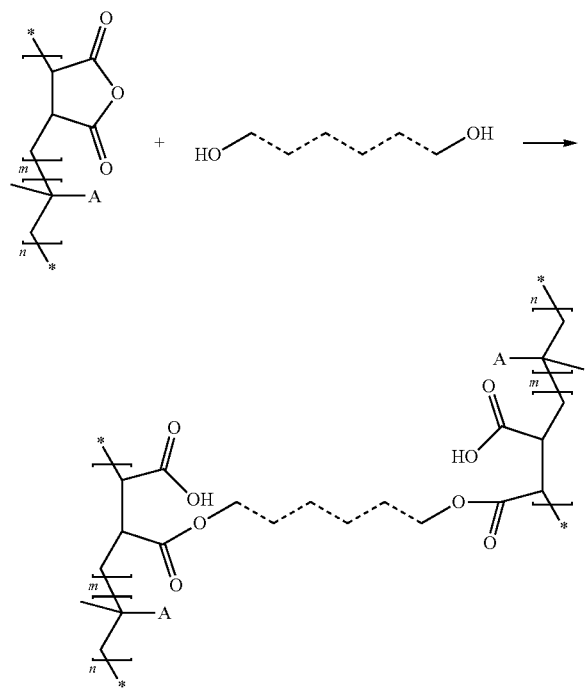

Such a crosslinked polymer is novel and thus also forms the subject of the present invention.

The crosslinked polymer may thus be obtained by reacting said polyol compound with the maleic anhydride ethylenic polymer described previously. Some or all of the anhydride groups react with the OH group of the polyol compound and form a unit bearing an ester group and a carboxylic acid group as described in scheme I.

The amine catalyst used in the process according to the invention may be chosen from catalysts bearing a primary amine function or bearing an aminidine function or bearing a guanidine function.

The catalyst bearing a tertiary amine function may be chosen from triethylamine, diisopropylethylamine, tri-n-propylamine, tri-n-butylamine, methyldibutylamine, N-methyldicyclohexylamine, N,N-dimethylcyclohexylamine, ethyldiisopropylamine, N,N-diethylcyclohexylamine, pyridine, 4-dimethylaminopyridine, N-methylpiperidine, N-ethylpiperidine, N-n-butylpiperidine, 1,2-dimethylpiperidine, N-methylpyrrolidine, 1,2-dimethylpyrrolidine, dimethylaniline, picoline, N,N-dimethylbenzylamine, bis(2-dimethylaminoethyl) ether, N,N,N',N',N''-pentamethyldiethylenetriamine, N,N,N',N'-tetramethylethylenediamine, N-methylmorpholine, N-ethylmorpholine and 1,4-diazabicyclo[2.2.2]octane, and mixtures thereof.

Diisopropylethylamine is preferably used.

The catalysts bearing an aminidine function are, for example, 1,5-diazabicyclo[4.3.0]non-5-ene (or DBN) and 1,8-diazabicyclo[5.4.0]undec-7-ene (or DBU).

The catalysts bearing a guanidine function may be chosen from the compounds of formula (V) below:

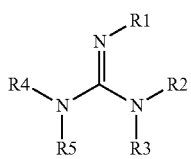

(V)

in which R1, R2, R3, R4 and R5 independently represent a hydrogen atom or a linear or branched C1-04 lower alkyl or alkenyl radical, when R1, R2 and R3 and R4 represent a hydrogen atom, R5 may also denote a radical from the following: acetyl; carboxamide; methoxy; ethoxy; 1,2,4-triazolyl; cyclopentyl; methoxycarbonyl; ethoxycarbonyl; phenyl; benzyl; thiazolidone; benzimidazole; benzoxazole; benzothiazole; or C(=NH)—NR6R7 in which R6 and R7 denote, independently of each other, a hydrogen atom or a linear or branched C1-04 lower alkyl radical; or else a phenyl radical, when R1=R2=R3=H, R4 and R5 may also form, with the nitrogen atom that bears them, a pyrrolidine, piperidine, pyrazole or 1,2,4-triazole ring, when R1=R2=H, and R4=H or methyl, R3 and R5 may also together form a 5-membered ring optionally containing an oxo group, and the organic or mineral salts thereof.

Salts that may be mentioned include the hydrochloride, sulfate, sulfamate, carbonate, bicarbonate, phosphate and acetate salts.

Among the compounds of formula (V), mention may be made especially of the following compounds:

guanidine, aminoguanidine, 1-acetylguanidine, guanylurea, phenylguanidine, 1,1-dimethylguanidine, 1-ethylguanidine, 1,1-diethylguanidine, creatine, agmatine, biguanide, N-methyl biguanide, N-ethyl biguanide, N-propyl biguanide, N-butylbiguanide, 1,1-dimethylbiguanide, 1-phenylbiguanide, 1,1,3,3-tetramethylguanidine, 2-tert-butyl-1,1,3,3-tetramethylguanidine, 1H-pyrazole-1-carboxamidine, 5-hydroxy-3-methyl-1H-pyrazole-1-carboximidamide, 3,5-diamino-1H-1,2,4-triazole-1-carboximidamide, 2-guanidone-4-thiazolidone, 2-guanidinobenzimidazole, 2-guanidinobenzoxazole, 2-guanidinobenzothiazole, 1,1,3,3-tetramethylguanidine (or TMG), 1,5,7-triazabicyclo[4.4.0]dec-5-ene (or TBD), 7-methyl-1,5,7-triazabicyclo[4.4.0]dec-5-ene (or MTBD).

The amine catalyst may be present in a content ranging from 0.1% to 0.5% by weight and preferably ranging from 0.1% to 0.2% by weight relative to the total weight of the composition derived from the extemporaneous mixing.

The process for treating keratin fibres, in particular human keratin fibres such as the hair, comprises:

(i) a step of applying to keratin fibres a mixture (extemporaneous) of the maleic anhydride ethylenic polymer, or of a cosmetic composition comprising it, of the liposoluble polyol compound or of a cosmetic composition containing it, and of the amine catalyst as defined previously;
(ii) a step of heating the keratin fibres to a temperature ranging from 90° C. to 250° C.;
steps (i) and (ii) being performed simultaneously or separately, in the order: step (i) and then step (ii).

According to one embodiment of the process according to the invention, the mixing of the composition comprising the maleic anhydride ethylenic polymer and of the liposoluble polyol, or of the composition containing it, and of the amine catalyst is performed in a time of between 1 minute and 24 hours before application to keratin fibres, and preferably between 5 and 30 minutes.

The process according to the invention comprises a step (ii) of heating the keratin fibres to a temperature ranging from 90° C. to 250° C., preferably ranging from 100 to 230° C. Preferably, the step of heating the keratin fibres is performed at a temperature ranging from 170 to 250° C., preferably ranging from 180° C. to 240° C., preferentially ranging from 190° C. to 230° C. and especially ranging from 200° C. to 230° C.

This heating step is advantageously performed using an iron.

The heating step is necessary to optimize the effects of the process.

For the purposes of the present invention, the term "iron" means a device for heating keratin fibres by placing said fibres and the heating device in contact with one another. The end of the iron which comes into contact with the keratin fibres generally has two flat surfaces. These two surfaces may be made of metal or ceramic. In particular, these two surfaces may be smooth or crimped or curved.

The heating step may be performed using a straightening iron, a curling iron or a crimping iron. Preferably, the heating step is performed using a straightening iron.

As examples of irons that may be used in the straightening process according to the invention, mention may be made of any type of flat iron, and in particular, in a nonlimiting manner, those described in patents U.S. Pat. Nos. 5,957,140 and 5,046,516.

The iron may be applied by successive separate strokes lasting a few seconds or by gradual movement or sliding along the locks of keratin fibres, especially of human keratin fibres such as the hair.

Preferably, the iron is applied in the process according to the invention by a continuous movement from the root to the tip of the hair, in one or more passes, in particular in two to twenty passes. The duration of each pass of the iron may last from 2 seconds to 1 minute.

The process according to the invention may also comprise an additional step of drying the keratin fibres after step (i) of applying the ethylenic polymer or the composition containing it and before step (ii) of heating the keratin fibres performed at a temperature ranging from 90° C. to 250° C. The drying step may be performed using a hairdryer or a hood or by leaving to dry naturally. The drying step is advantageously performed at a temperature ranging from 20 to 70° C.

After the heating step, the keratin fibres may be optionally rinsed with water or washed with a shampoo. The keratin fibres are then optionally dried using a hairdryer or a hood or left to dry naturally.

According to one embodiment, the process according to the invention is performed on natural or damaged or sensitized keratin fibres, which have optionally been dyed and/or have optionally undergone a prior long-lasting or temporary shaping treatment.

Damaged fibres are, for example, dry or coarse or brittle or split or soft fibres.

Sensitized fibres are, for example, bleached, relaxed or permanent-waved fibres.

The process according to the invention is preferably performed on dry keratin fibres, i.e. fibres that are not wet, especially dry hair.

After step (i) of applying to the keratin fibres the ethylenic polymer or a cosmetic composition containing it, and before performing step (ii) of heating the keratin fibres, the ethylenic polymer or the composition containing it may be left on the fibres for a time ranging from 1 to 60 minutes, preferably ranging from 2 to 50 minutes and preferentially ranging from 5 to 45 minutes. The leave-on time may take place at a temperature ranging from 15° C. to 45° C., preferably at room temperature (25° C.).

The composition described previously is advantageously applied to the keratin fibres in an amount ranging from 0.1 to 10 grams and preferably from 0.2 to 5 grams of composition per gram of keratin fibres.

After application of the composition to the keratin fibres, they may be drained to remove the excess composition.

The treatment process according to the invention may be performed during and/or after, preferably after, an additional process of cosmetic treatment of the keratin fibres, such as a process for temporarily shaping (shaping with curlers, a curling iron or a straightening iron) or a process for durably shaping (permanent-waving or relaxing) or a process for dyeing or bleaching the keratin fibres.

The treatment process according to the invention may also be performed as a post-treatment to a cosmetic treatment process.

In particular, the treatment process is performed as a post-treatment to a dyeing, bleaching or relaxing process and/or a permanent-waving process.

According to the process according to the invention, mixing, especially extemporaneous mixing, of the maleic anhydride ethylenic polymer, the liposoluble polyol compound and the amine catalyst is performed, and the mixture is applied to the keratin fibres, in particular to the hair.

The composition used according to the invention is generally suitable for topical application to keratin fibres, and thus generally comprises a physiologically acceptable medium, i.e. a medium that is compatible with the skin and/or its integuments. It is preferably a cosmetically acceptable medium, i.e. a medium which has a pleasant colour, odour and feel and which does not cause any unacceptable discomfort (stinging, tautness or redness) liable to discourage the consumer from using this composition.

According to a preferred embodiment of the invention, the composition comprising the maleic anhydride ethylenic polymer may contain a hydrocarbon-based oil.

The hydrocarbon-based oil is an oil that is liquid at room temperature (25° C.).

The term "hydrocarbon-based oil" means an oil formed essentially from, or even consisting of, carbon and hydrogen atoms, and optionally oxygen and nitrogen atoms, and not containing any silicon or fluorine atoms. It may contain alcohol, ester, ether, carboxylic acid, amine and/or amide groups.

The hydrocarbon-based oil may be volatile or non-volatile. Preferably, the hydrocarbon-based oil is volatile.

The hydrocarbon-based oil may be chosen from:
hydrocarbon-based oils containing from 8 to 14 carbon atoms, and especially:
- branched $C_8$-$C_{14}$ alkanes, for instance $C_8$-$C_{14}$ isoalkanes of petroleum origin (also known as isoparaffins), for instance isododecane (also known as 2,2,4,4,6-pentamethylheptane), isodecane and, for example, the oils sold under the trade name Isopar or Permethyl,
- linear alkanes, for instance n-dodecane (C12) and n-tetradecane (C14) sold by Sasol under the respective references Parafol 12-97 and Parafol 14-97, and also mixtures thereof, the undecane-tridecane mixture, the mixtures of n-undecane (C11) and of n-tridecane (C13) obtained in Examples 1 and 2 of patent application WO 2008/155 059 from the company Cognis, and mixtures thereof,
- short-chain esters (containing from 3 to 8 carbon atoms in total) such as ethyl acetate, methyl acetate, propyl acetate or n-butyl acetate,
- hydrocarbon-based oils of plant origin such as triglycerides consisting of fatty acid esters of glycerol, the fatty acids of which may have chain lengths varying from $C_4$ to $C_{24}$, these chains possibly being linear or branched, and saturated or unsaturated; these oils are especially heptanoic or octanoic acid triglycerides, or alternatively wheatgerm oil, sunflower oil, grapeseed oil, sesame seed oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin oil, sesame oil, marrow oil, rapeseed oil, blackcurrant oil, evening primrose oil, millet oil, barley oil, *quinoa* oil, rye oil, safflower oil, candlenut oil, passionflower oil and musk rose oil; shea butter; or else caprylic/capric acid triglycerides, for instance those sold by the company Stéarineries Dubois or those sold under the names Miglyol 810®, 812® and 818® by the company Dynamit Nobel,
- synthetic ethers having from 10 to 40 carbon atoms;
- linear or branched hydrocarbons of mineral or synthetic origin, such as petroleum jelly, polydecenes, hydrogenated polyisobutene such as Parleam®, squalane and liquid paraffins, and mixtures thereof,
- synthetic esters such as oils of formula $R_1COOR_2$ in which $R_1$ represents a linear or branched fatty acid residue containing from 1 to 40 carbon atoms and $R_2$ represents an, in particular, branched hydrocarbon-based chain containing from 1 to 40 carbon atoms, on condition that $R_1+R_2$ 10, for instance purcellin oil (cetostearyl octanoate), isopropyl myristate, isopropyl palmitate, $C_{12}$ to $C_{15}$ alkyl benzoates, hexyl laurate, diisopropyl adipate, isononyl isononanoate, 2-ethylhexyl palmitate, isostearyl isostearate, 2-hexyldecyl laurate, 2-octyldecyl palmitate, 2-octyldodecyl myristate, alkyl or polyalkyl heptanoates, octanoates, decanoates or ricinoleates such as propylene glycol dioctanoate; hydroxylated esters such as isostearyl lactate, diisostearyl malate and 2-octyldodecyl lactate; polyol esters and pentaerythritol esters,
- fatty alcohols that are liquid at room temperature, with a branched and/or unsaturated carbon-based chain containing from 12 to 26 carbon atoms, for instance octyldodecanol, isostearyl alcohol, oleyl alcohol, 2-hexyldecanol, 2-butyloctanol and 2-undecylpentadecanol.

Advantageously, the hydrocarbon-based oil is apolar (thus formed solely from carbon and hydrogen atoms).

The hydrocarbon-based oil is preferably chosen from hydrocarbon-based oils containing from 8 to 14 carbon atoms, in particular the apolar oils described previously.

Preferentially, the hydrocarbon-based oil is isododecane.

The composition comprising the polymer may contain, in addition to the hydrocarbon-based oil, a silicone oil. The term "silicone oil" means an oil comprising at least one silicon atom and especially at least one Si—O group. The silicone oil may be volatile or non-volatile.

The term "volatile oil" means an oil (or non-aqueous medium) that is capable of evaporating on contact with the skin in less than one hour, at room temperature and at atmospheric pressure. The volatile oil is a volatile cosmetic oil, which is liquid at room temperature, especially having a non-zero vapour pressure, at room temperature and at atmospheric pressure, in particular having a vapour pressure ranging from 0.13 Pa to 40 000 Pa ($10^{-3}$ to 300 mmHg), preferably ranging from 1.3 Pa to 13 000 Pa (0.01 to 100 mmHg) and preferentially ranging from 1.3 Pa to 1300 Pa (0.01 to 10 mmHg).

The term "non-volatile oil" means an oil with a vapour pressure of less than 0.13 Pa.

Volatile silicone oils that may be mentioned include volatile linear or cyclic silicone oils, especially those with a viscosity ≤8 centistokes (cSt) ($8\times10^{-6}$ m$^2$/s), and especially having from 2 to 10 silicon atoms and in particular from 2 to 7 silicon atoms, these silicones optionally comprising alkyl or alkoxy groups having from 1 to 10 carbon atoms. As volatile silicone oil that may be used in the invention, mention may be made especially of dimethicones with viscosities of 5 and 6 cSt, octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

As non-volatile silicone oils, mention may be made of linear or cyclic non-volatile polydimethylsiloxanes (PDMSs); polydimethylsiloxanes comprising alkyl, alkoxy or phenyl groups, which are pendant or at the end of a silicone chain, these groups containing from 2 to 24 carbon atoms; phenyl silicones, for instance phenyl trimethicones, phenyl dimethicones, phenyltrimethylsiloxydiphenylsiloxanes, diphenyl dimethicones, diphenylmethyldiphenyltrisiloxanes and 2-phenylethyl trimethylsiloxysilicates.

Advantageously, the composition may comprise a hydrocarbon-based oil in a content ranging from 60% to 100% by weight relative to the total weight of the oils present in the composition and from 0 to 40% by weight of silicone oil. According to a preferred embodiment of the invention, the composition contains as oil only a hydrocarbon-based oil. Preferentially, the hydrocarbon-based oil is volatile.

The composition according to the invention may comprise a cosmetic additive chosen from fragrances, preserving agents, fillers, UV-screening agents, oils, waxes, surfactants, moisturizers, vitamins, ceramides, antioxidants, free-radical scavengers, polymers, thickeners, dyestuffs and antidandruff active agents.

According to one embodiment, the composition used according to the invention is an anhydrous composition. The term "anhydrous composition" means a composition containing less than 2% by weight of water, or even less than 0.5% of water, and is especially free of water. Where appropriate, such small amounts of water may especially be introduced by ingredients of the composition that may contain residual amounts thereof.

The invention will now be described with reference to the following examples, which are given as non-limiting illustrations.

EXAMPLE 1

2-Ethylhexyl acrylate/maleic anhydride copolymer (85/15 by Weight)—Polymer 1

170 g of 2-ethylhexyl acrylate and 30 g of maleic anhydride were placed in a jacketed 1-litre reactor equipped with a stirring anchor. A mixture of 210 g of isododecane and 90 g of ethyl acetate was then added.

The reaction medium was brought to a temperature of 40° C. with stirring (150 rpm) and was sparged with argon for 10 minutes, followed by addition of 2 g of initiator tert-butyl peroxy-2-ethylhexanoate (Trigonox® 21S from Akzo Nobel).

The heating of the jacket was set at 90° C. for 7 hours at 150 rpm.

The medium was then diluted with 300 g of isododecane, and then concentrated by distillation to remove the ethyl acetate and the unreacted maleic anhydride.

A solution containing 30% by weight of the copolymer in isododecane was finally obtained.

The polymer obtained has a molecular weight (Mw) of about 12 000 g/mol.

EXAMPLE 2

2-Ethylhexyl acrylate/maleic anhydride copolymer (80/20 by Weight)—Polymer 2

The polymer was prepared according to the procedure of Example 1, using 160 g of 2-ethylhexyl acrylate and 40 g of maleic anhydride.

A solution containing 32% by weight of the copolymer in isododecane (yield of greater than 90%) was finally obtained.

The polymer obtained has a molecular weight (Mw) of about 15 000 g/mol.

EXAMPLE 3

2-Ethylhexyl acrylate/pdms methacrylate/maleic anhydride copolymer (50/30/20 by Weight)—Polymer 3

The polymer was prepared according to the procedure of Example 1, using:
40 g of maleic anhydride with 28 g of isododecane and 21 g of ethyl acetate;
sparging with argon, followed by addition over 1 hour of a mixture of 100 g of 2-ethylhexyl acrylate, 60 g of PDMS methacrylate (X-22-2426 from Shin-Etsu; size of the PDMS chain=12 000 g/mol), 168 g of isododecane, 72 g of ethyl acetate and 2 g of Trigonox® 21S.

A solution containing 40% by weight of the copolymer in isododecane was finally obtained.

EXAMPLE 4

2-Ethylhexyl acrylate/stearyl acrylate/maleic anhydride copolymer (50/30/20 by Weight)—Polymer 4

The polymer was prepared according to the procedure of Example 1, using:
20 g of 2-ethylhexyl acrylate and 20 g of maleic anhydride.
40 g of maleic anhydride with 28 g of isododecane and 21 g of ethyl acetate;
sparging with argon, followed by addition over 1 hour of a mixture of 100 g of 2-ethylhexyl acrylate, 60 g of stearyl methacrylate, 168 g of isododecane, 72 g of ethyl acetate and 2 g of Trigonox® 21S.

A solution containing 41% by weight of the copolymer in isododecane was finally obtained.

The polymer obtained has a molecular weight (Mw) of close to 17 000 g/mol.

COMPARATIVE EXAMPLES 3 TO 7

The six compositions described below were prepared (weight percentages).

For each composition, all the ingredients were mixed at the same time at room temperature (25° C.) in a glass flask and the composition was then heated at 150° C. using a multi-well stirrer for 10 minutes. The state of the composition was then observed by turning the flask upside-down to thus determine whether the mixture reacted with a crosslinking reaction of the polymer (crosslinking inducing an increase in the viscosity of the initial mixture).

The following results were obtained:

|  | Example 3 | Example 4 | Example 5 |
|---|---|---|---|
| Polymer of Example 2 | 25% AM | 25% AM | 25% AM |
| Diol 1 | 10% | 10% | 10% |
| Diisopropylethylamine | 0% | 0.15% | 0.5% |
| Isododecane | qs 100% | qs 100% | qs 100% |
| State of the composition | Fluid | Set to a solid; does not flow | Set to a solid; does not flow |

Diol 1: hydrogenated dihydroxylated polybutene GI-1000 from Nisso (hydroxyl number: 60-75 KOH mg/number-average = number-average molecular weight = 1500)

|  | Example 6 | Example 7 | Example 8 |
|---|---|---|---|
| Polymer of Example 2 | 25% AM | 25% AM | 25% AM |
| Diol 2 | 10% | 10% | 10% |
| Diisopropylethylamine | 0% | 0.15% | 0.5% |
| Isododecane | qs 100% | qs 100% | qs 100% |
| State of the composition | Fluid | Set to a solid; does not flow | Set to a solid; does not flow |

Diol 2: PDMS-diOH KF-6001 from Shin-Etsu (hydroxyl number = 62 mg KOH/g; viscosity at 25° C. = 45 mm$^2$/s)

The results obtained show that the compositions according to the invention (Examples 4, 5, 7, 8) thickened after heating, which proves that the crosslinking reaction of the polymer with the diol has indeed taken place.

The same test performed without catalyst (Examples 3, 6) or without performing the heating step for 10 minutes at 150° C., leads to compositions that are all fluid: without the heating step, crosslinking of the polymer does not take place. Similarly, without the catalyst, crosslinking of the polymer does not take place.

COMPARATIVE EXAMPLES 9 AND 10

The following two compositions were prepared (weight percentages):

|  | Example 9 | Example 10 |
|---|---|---|
| Polymer of Example 2 | 10% AM | — |
| Polymer of Example 3 | — | 10% AM |

|   | Example 9 | Example 10 |
|---|---|---|
| Diol 1 |  | 5% |
| Diol 2 | 5% | — |
| Diisopropylethylamine | 0.15% | 0.15% |
| Isododecane | qs 100% | qs 100% |

Locks of hair were treated according to the following protocol:
2.7 g locks of natural Caucasian hair were used.

The locks were washed with Ultra Doux camomile shampoo (from La Scad) by applying 1.2 g of shampoo to a lock of wet hair. The lock was then rinsed, then drained, then dried under a hood at 60° C. for 10 minutes.

5.4 g of the test composition were then applied to the lock of hair. The lock was then dried at 60° C. (under a hood) for 15 minutes, and a straightening iron heated to 210° C. was then applied for 15 minutes by making 15 sweeps along the length of the lock (each sweep lasting about 4 seconds). The fixing quality of the lock was evaluated.

Washing with water was then performed by immersing the lock of treated hair in water (at room temperature, 25° C.) for 5 minutes. The lock was then drained and then dried under a hood at 60° C. for 15 minutes. The fixing quality of the lock of hair was again evaluated.

For comparison of the effect of the heating step performed with the curling iron heated to 210° C., the same protocol is performed on another lock of hair, but without performing the application of the curling iron.

The fixing quality of the lock of hair was evaluated by observing the more or less rigid appearance of the lock: the lock is taken by one of its ends with the fingers and turned upside-down, holding it at the bottom; the shape of the lock is then observed; either the lock retains its shape, which means that the lock is fixed very well; or the lock becomes deformed (under the effect of gravity) which means that the lock is not fixed very well.

The fixing quality of the lock of hair was evaluated according to the following grading:
Lock without fixing: −
Lock with weak fixing: +
Lock with moderate fixing: ++
Lock with very good fixing: +++

The following results were obtained:

|   | Example 9 with heat | Example 9' without heat | Example 10 with heat | Example 10' without heat |
|---|---|---|---|---|
| Fixing before washing | +++ | + | +++ | + |
| Fixing after washing | ++ | + | ++ | + |

The results obtained show that the locks of Examples 9 and 10 treated via the process according to the invention have good fixing properties before and after washing with water. These properties are superior to those of the locks of Examples 9' and 10' which did not undergo a heating step with the curling iron.

EXAMPLE 11

The following composition is prepared (weight percentage):

| Polymer 1 (Example 1) | 8% |
|---|---|
| Hydrogenated dihydroxylated polybutene | 4% |
| (GI-1000 from Nisso) |  |
| Diisopropylethylamine | 0.12% |
| Isododecane | qs 100% |

The composition is applied to the hair, left to dry for 15 minutes at room temperature, and the curling iron heated to 210° C. is then applied to the locks.

The hair thus treated has good, water-resistant fixing.

EXAMPLE 12

The following composition is prepared (weight percentage):

| Polymer 4 (Example 4) | 6% |
|---|---|
| Hydrogenated dihydroxylated polybutene | 3% |
| PDMS-diOH KF-6001 from Shin-Etsu |  |
| Diisopropylethylamine | 0.09% |
| Isododecane | qs 100% |

The composition is applied to the hair, left to dry for 15 minutes at room temperature, and the curling iron heated to 210° C. is then applied to the locks.

The hair thus treated has good, water-resistant fixing.

EXAMPLE 13

The following composition is prepared (weight percentage):

| Polymer 4 (Example 4) | 6% |
|---|---|
| 1,12-Dodecanediol | 2% |
| Diisopropylethylamine | 0.09% |
| Isododecane | qs 100% |

The composition is applied to the hair, left to dry for 15 minutes at room temperature, and the curling iron heated to 210° C. is then applied to the locks.

The hair thus treated has good, water-resistant fixing.

The invention claimed is:

1. A cosmetic process for treating keratin fibres, comprising:
   (i) a step of applying to keratin fibres an extemporaneous mixture of a maleic anhydride ethylenic polymer, or of a cosmetic composition comprising it, of a liposoluble polyol compound or of a cosmetic composition containing it, and of an amine catalyst;
   said maleic anhydride ethylenic polymer being derived from the polymerization of:
   (a) 45% to 95% by weight, relative to the total weight of monomers, of an ethylenic monomer bearing an at least C8 linear or branched alkyl group chosen from:
     a) linear or branched C8-C22 alkyl (meth)acrylates;
     b) the (meth)acrylamides of formula $CH_2=C(R1)-CONR3R4$ in which R1 represents a hydrogen atom or a methyl radical, R3 represents a hydrogen atom or a linear or branched C1-C12 alkyl group, and R4 represents a linear or branched C8 to C12 alkyl group;
     c) the vinyl esters of formula $R5-CO-O-CH=CH_2$ in which R5 represents a linear or branched C8-C22 alkyl group; and d) the ethers of formula R6-O—CH=CH2 in which R6 represents a linear or branched C8-C22 alkyl group;
(b) 5% to 25% by weight of maleic anhydride;
(c) 0% to 50% by weight of additional monomer chosen from:
(i) polydimethylsiloxane silicone monomers bearing a mono(meth)acryloyloxy end group of formula (I) below:

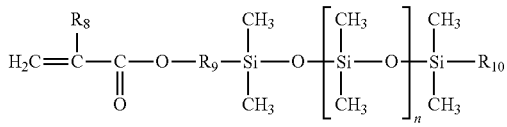

in which:
R8 denotes a hydrogen atom or a methyl group;
R9 denotes a linear or branched divalent hydrocarbon-based group containing from 1 to 10 carbon atoms and optionally containing one or two ether bonds —O—;
R10 denotes a linear or branched alkyl group containing from 1 to 10 carbon atoms
n denotes an integer ranging from 1 to 300;
(ii) linear or branched C1-C6 alkyl (meth)acrylate or C6-C12 cycloalkyl (meth)acrylate non-silicone monomers;
(ii) a step of heating the keratin fibres to a temperature ranging from 90° C. to 250° C.;
steps (i) and (ii) being performed at the same time or separately, in the order (i) and then (ii).

2. The process according to claim 1, wherein the ethylenic monomer bearing an at least C8 linear or branched alkyl group is chosen from C8-C22.

3. The process according to claim 1, wherein the ethylenic monomer bearing an at least C8 linear or branched alkyl group is chosen from 2-ethylhexyl acrylate, 2-ethylhexyl methacrylate, lauryl acrylate, lauryl methacrylate, behenyl acrylate, behenyl methacrylate, stearyl acrylate, stearyl methacrylate.

4. The process according to claim 1, wherein the ethylenic monomer bearing an at least C8 linear or branched alkyl group is present in said ethylenic polymer in a content ranging from 50% to 90% by weight, relative to the total weight of monomers.

5. The process according to claim 1, wherein- maleic anhydride is present in said ethylenic polymer in a content ranging from 10% to 25% by weight relative to the total weight of monomers.

6. The process according to claim 1, wherein, for said silicone monomer of formula (I):
R8 denotes a methyl group;
R9 denotes a linear divalent hydrocarbon-based group containing from 2 to 4 carbon atoms;
R10 represents a linear or branched alkyl group, comprising from 2 to 8 carbon atoms;
n denotes an integer ranging from 3 to 200.

7. The process according to claim 1, wherein said additional monomer is non-silicone and is chosen from C6-C12 cycloalkyl (meth)acrylates.

8. The process according to claim 1, wherein said ethylenic polymer comprises said additional silicone monomer of formula (I).

9. The process according to claim 1, wherein said ethylenic polymer comprises an additional monomer present in a content ranging from 5% to 50% by weight, relative to the total weight of monomers.

10. The process according to claim 1, wherein said ethylenic polymer does not contain any additional monomer.

11. The process according to claim 1, wherein said ethylenic polymer comprises, or consists of:
(a) 75% to 95% by weight, relative to the total weight of monomers, of linear or branched C8-C22 alkyl (meth)acrylate;
(b) 5% to 25% by weight of maleic anhydride.

12. The process according to claim 1 said ethylenic polymer is chosen from the following copolymers:
2-ethylhexyl acrylate/maleic anhydride
stearyl acrylate/maleic anhydride
2-ethylhexyl acrylate/stearyl acrylate/maleic anhydride.

13. The process according to claim 1, wherein said ethylenic polymer comprises, or consists of:
(a) 45% to 94.5% by weight, relative to the total weight of monomers, of linear or branched C8-C22 alkyl (meth)acrylate;
(b) 5% to 25% by weight of maleic anhydride;
(c) 0.5% to 50% by weight of silicone monomer (I).

14. The process according to claim 1, wherein said ethylenic polymer is chosen from the following copolymers:
2-ethylhexyl acrylate/maleic anhydride/silicone monomer (I)
stearyl acrylate/maleic anhydride/silicone monomer (I)
2-ethylhexyl acrylate/stearyl acrylate/maleic anhydride/silicone monomer (I).

15. The process according to claim 1, wherein said ethylenic polymer comprises, or consists of:
(a) 45% to 94.5% by weight, relative to the total weight of monomers, of linear or branched C8-C18 alkyl (meth)acrylate;
(b) 5% to 25% by weight of maleic anhydride;
(c) 0.5% to 50% by weight of C6-C12 cycloalkyl (meth)acrylate.

16. The process according to claim 1, wherein said ethylenic polymer is chosen from the following copolymers:
2-ethylhexyl acrylate/maleic anhydride/isobornyl (meth)acrylate
stearyl acrylate/maleic anhydride/isobornyl (meth)acrylate
2-ethylhexyl acrylate/stearyl acrylate/maleic anhydride/isobornyl (meth)acrylate.

17. The process according to claim 1, wherein said ethylenic polymer comprises, or consists of:
(a) 45% to 94.5% by weight, relative to the total weight of monomers, of linear or branched C8-C18 alkyl (meth)acrylate;
(b) 5% to 25% by weight of maleic anhydride;
(c) 0.5% to 50% by weight of a mixture of C6-C12 cycloalkyl (meth)acrylate and of silicone monomer (I).

18. The process according to claim 1, wherein said ethylenic polymer is chosen from the following copolymers:
2-ethylhexyl acrylate/maleic anhydride/isobornyl (meth)acrylate/silicone monomer (I)
stearyl acrylate/maleic anhydride/isobornyl (meth)acrylate/silicone monomer (I)
2-ethylhexyl acrylate/stearyl acrylate/maleic anhydride/isobornyl (meth)acrylate/silicone monomer (I).

19. The process according to claim 1, wherein the ethylenic polymer has a weight-average molecular weight ranging from 5000 to 1 000 000 g/mol.

20. The process according to claim 1, wherein the liposoluble polyol is a non-polymeric organic compound of formula (II):

W(OH)$n$     (II)

in which n denotes an integer greater than or equal to 2, W denotes a linear or branched or (hetero)cyclic, saturated or unsaturated C8-C30 multivalent radical, W also optionally bearing one or more functions chosen from ether, thioether, ester, ketone and amide functions.

21. The process according to claim 1, wherein the liposoluble polyol is a diol bearing a C8-C18 hydrocarbon-based chain.

22. The process according to claim 1, wherein the polyol is chosen from polyolefin diols, polydimethylsiloxane diols and polyester diols.

23. The process according to claim 1, wherein the liposoluble polyol is used in a mole ratio of OH group of the liposoluble polyol/maleic anhydride group of the ethylenic polymer ranging from 0.01 to 10.

24. The process according to claim 1, wherein the amine catalyst is chosen from catalysts bearing a primary amine function or bearing an aminidine function or bearing a guanidine function.

25. The process according to claim 1, wherein the amine catalyst is present in a content ranging from 0.1% to 0.5% by weight relative to the total weight of the composition derived from said mixture.

26. The process according to claim 1, wherein the composition comprises a hydrocarbon-based oil.

27. The process according to claim 1, wherein the mixing of the composition comprising the block polymer of maleic anhydride and of the liposoluble polyol, or of the composition containing it, and of the amine catalyst is performed in a time of between 1 minute and 24 hours before application to keratin fibres.

28. The process according to claim 1, wherein the heating step is performed at a temperature ranging from 100 to 230° C.

29. The process according to claim 1, wherein the heating step is performed using an iron.

30. The process according to claim 1, which comprises an additional step of drying the keratin fibres after step (i) and before step (ii).

* * * * *